(12) United States Patent
Halsmer et al.

(10) Patent No.: US 7,682,077 B2
(45) Date of Patent: Mar. 23, 2010

(54) METHOD AND APPARATUS FOR DRIVING A MOBILE IMAGING SYSTEM

(75) Inventors: Matthew Aaron Halsmer, Westfield, IN (US); Jonathan M. Butzine, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 134 days.

(21) Appl. No.: 12/138,195

(22) Filed: Jun. 12, 2008

(65) Prior Publication Data

US 2009/0310753 A1 Dec. 17, 2009

(51) Int. Cl.
*H05G 1/02* (2006.01)
*A61B 6/08* (2006.01)

(52) U.S. Cl. .................................. 378/198; 378/205

(58) Field of Classification Search ............ 378/198, 378/205
See application file for complete search history.

(56) References Cited

U.S. PATENT DOCUMENTS

| | | | |
|---|---|---|---|
| 4,697,661 A | 10/1987 | Pajerski et al. | |
| 4,829,844 A | 5/1989 | Boomgaarden et al. | |
| 5,351,282 A * | 9/1994 | Kadowaki et al. | 378/198 |
| 5,425,069 A * | 6/1995 | Pellegrino et al. | 378/198 |
| 6,409,382 B1 | 6/2002 | Akutsu et al. | |
| 6,422,747 B2 | 7/2002 | Akutsu et al. | |
| 6,705,758 B1 * | 3/2004 | Luusua et al. | 378/198 |
| 6,871,715 B1 * | 3/2005 | Diaz Carmena et al. | 180/65.51 |
| 7,298,825 B2 | 11/2007 | Omernick et al. | |

* cited by examiner

*Primary Examiner*—Allen C. Ho
(74) *Attorney, Agent, or Firm*—Dean Small; Small Patent Law Group

(57) ABSTRACT

A mobile imaging system comprises a motorized drive assembly having first and second drive wheels that are coupled to the motorized drive assembly. A column is coupled to and extends upwardly from the motorized drive assembly and is rotatable around a pivot point. An arm is coupled to the column and includes a radiation source mounted on an outer end thereof. A longitudinal axis extends parallel to the length of the mobile imaging system and is centered between the first and second drive wheels. A controller is configured to determine first and second velocities to drive the first and second drive wheels based on an angle of rotation of the column with respect to the longitudinal axis.

20 Claims, 2 Drawing Sheets

METHOD AND APPARATUS FOR DRIVING A MOBILE IMAGING SYSTEM

BACKGROUND OF THE INVENTION

This invention relates generally to mobile imaging systems, and more particularly to positioning a mobile imaging system prior to scanning a patient.

Mobile x-ray systems, as well as other diagnostic imaging devices, are often mounted on motorized carts that are driven to the patient's location. The cart typically has two main wheels in the rear that are driven to move the system. Two swivel wheels are usually provided in the front of the cart. Additionally, the x-ray source or tube is mounted on a swivel column proximate the front of the unit.

In these mobile imaging systems, the movable unit or cart has independently driven wheels that allow for some degree of steering. A drive handle may be provided at the rear of the cart, allowing the operator to push harder on one side or the other of the handle, resulting in the cart turning one direction or the other.

Using the rear drive handle, the operator can drive to a location, position the cart proximate to the patient's bed, and position the x-ray source or other detector to images for example, the anatomy of interest. When positioning the x-ray tube, the operator is often at the tube-side of the system, which may be on the other side of the patient's bed from the movable unit. Therefore, if the movable unit is not in the correct position, the operator has to return to the back side of the cart and attempt to position the unit such that the x-ray source is properly aligned with the anatomy. However, it can be challenging to position the mobile system from the rear drive handle as the unit is very heavy and not easily maneuverable within small distances. This adjustment process also can be very time consuming. In addition, some patient rooms are quite small and/or the available area in which to move the system is limited, such as by other patient monitoring devices and machines.

Therefore, a need exists for more easily positioning the x-ray source with respect to the anatomy.

BRIEF DESCRIPTION OF THE INVENTION

In one embodiment, a mobile imaging system comprises a motorized drive assembly. First and second drive wheels are coupled to the motorized drive assembly. A column is coupled to and extends upwardly from the motorized drive assembly and is rotatable around a pivot point. An arm is coupled to the column and includes a radiation source mounted on an outer end thereof. A longitudinal axis extends parallel to the length of the mobile imaging system and is centered between the first and second drive wheels. A controller is configured to determine first and second velocities to drive the first and second drive wheels based on an angle of rotation of the column with respect to the longitudinal axis.

In another embodiment, a method for driving a mobile imaging system comprises defining a longitudinal axis that is centered between first and second drive wheels of a motorized drive assembly and is parallel to a length of the mobile imaging system. A pivot point is defined at a center of a rotatable column that is coupled to the motorized drive system and comprises an arm mounted thereto. An angle of rotation of the column is identified with respect to the longitudinal axis. First and second velocities are calculated to drive the first and second drive wheels based on the angle of rotation.

In yet another embodiment, a mobile x-ray system comprises a motorized drive assembly comprising first and second drive wheels. A column is mounted to the motorized drive assembly at a pivot point and comprises an arm mounted thereto. The column is rotatable with respect to the pivot point. A longitudinal axis extends parallel to a length of the mobile x-ray system and is centered between the first and second drive wheels. An x-ray source is mounted at an outer end of the arm. A collimator is mounted with respect to the x-ray source and is rotatable with respect to the x-ray source. A controller is configured to determine first and second velocities to drive the first and second drive wheels. The first and second velocities are based on at least one of an angle of rotation of the column with respect to the longitudinal axis and an angle of rotation of the collimator with respect to the longitudinal axis.

DETAILED DESCRIPTION OF THE INVENTION

Figure 1:
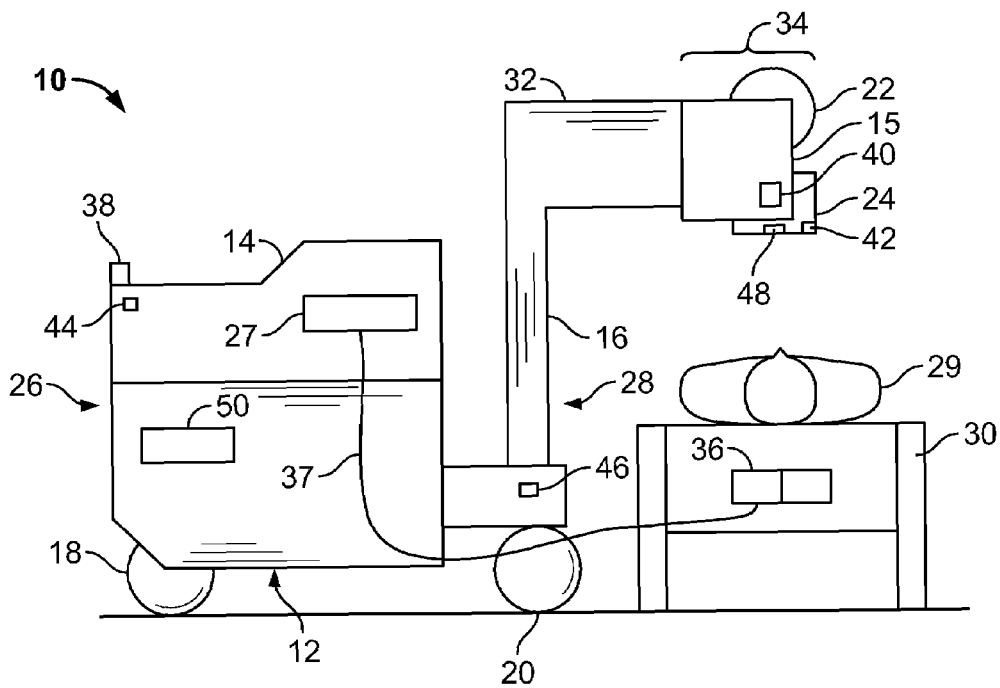
FIG. 1 is an elevation view of a mobile imaging system formed in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

FIG. 1 illustrates a mobile imaging system 10 that may be used in the medical field or in other fields. The system 10 has a wheeled motorized drive assembly 12 and an operator console 14 that may be supported by the drive assembly 12. The motorized drive assembly 12 has two rear drive wheels 18 (one wheel is shown) at a rear end 26 of the system 10 and two front wheels 20 (one wheel is shown) at a front end 28 of the system 10.

A column 16 or other support member is attached to, and extends upwardly from, the drive assembly 12 and rotates or swivels with respect to the drive assembly 12. A sensor 46 may detect the amount of rotation or movement of the column 16 with respect to the drive assembly 12. An arm 32 is fixed to the column 16 at a predetermined rotational position. The arm 32 may also telescope with respect to the column 16, allowing components mounted at an outer end of the arm 32 to be moved closer to or further away from the column 16. In one embodiment, the arm 32 may have further degrees of freedom with respect to the column 16. A radiation source 34, such as an x-ray source assembly 15, is attached to the outer end of the arm 32 and has an x-ray tube housing 22 containing an x-ray source (not shown). A collimator 24 is attached to the tube housing 22 and is rotatable with respect to the tube housing 22. A sensor 48 may be provided to detect the amount of rotation or movement of the collimator 24 with respect to the drive assembly 12 and/or column 16. An x-ray detector 36 detects x-ray data and may communicate with an imaging controller 27 wirelessly or over a cable 37.

It should be noted that the sensors of the various embodiments may be any type or types of sensors. For example, one or more of the sensors may operate based on sensing a change in distance using optical, magnetic, electrical, or other means.

A drive handle 38 is provided on the rear end 26 of the system 10. A drive controller 50 senses or receives signals based on the manipulation of the drive handle 38, and thus the system 10 may be driven to different locations to image a subject 29. The drive assembly 12 may have at least one motor and is capable of driving the first and second drive wheels 100 and 102 separately.

The subject 29 is typically lying on a bed or table 30. Once the system 10 is positioned near the table 30, the column 16 is swiveled or rotated to position the x-ray source assembly 15 over the subject 29. The detector 36 is positioned on the opposite side of the subject 29.

One or more user interfaces may be provided proximate the x-ray source assembly 15 and/or rear end 26 of the system 10 to align the desired anatomy within the subject 29 and the x-ray source assembly 15 based on the angle of rotation of the column 16, the collimator 24 and/or other desired direction of travel with respect to the drive assembly 12. The user interfaces may thus provide a plurality of inputs so that an operator can initiate motion in different desired directions. For example, a user interface 40 or 42 may be provided on the x-ray source assembly 15 or collimator 24, respectively. Alternatively, a user interface (not shown) may be provided on one or both sides of the arm 32. The user interfaces 40 and 42 communicate with the drive controller 50, allowing the user to adjust the position of the x-ray source assembly 15 relative to the anatomy of the subject 29 from the front end 28. In another embodiment, an additional user interface 44 may be provided proximate the rear end 26 of the system 10. Optionally, the user interface 44 may be integrated with the drive handle 38 or the user interfaces 40-44 may be configured as a remote control that may be held in the operator's hand away from the system 10. The user interfaces 40-44 may communicate with the drive controller 50 wirelessly or over a wired connection. The user interfaces 40-44 may be one of, or a combination of, a button, joystick, toggle switch, power assist handle, provided as a key on a keyboard or a selection on a touchscreen, and the like.

The drive controller 50 receives angle information from the sensor 46 and the sensor 48 that indicates the position of the column 16, arm 32, collimator 24, and/or x-ray source assembly 15. When the operator activates one of the user interfaces 40-44, the system 10 may be moved based on, for example, the angle of rotation of the column 16 with respect to the drive assembly 12. In another embodiment, the collimator 24 may be rotated or adjusted with respect to the x-ray tube housing 22. Therefore, the angle relationship between the collimator 24 and the drive assembly 12 will also change. The drive controller 50 may then move the system 10 (e.g., engage motor(s) within the drive assembly 12 to cause the rear drive wheels 18 to move and/or rotate the column 16) based on the angle of rotation of the collimator 24 with respect to the drive assembly 12. It should be understood that different angles of rotation with respect to the drive assembly 12 may be used. A technical effect of at least one embodiment is the ability to move the motorized cart-based system 10 based on an angular relationship between a component of the system 10 and the drive assembly 12.

Figure 2:
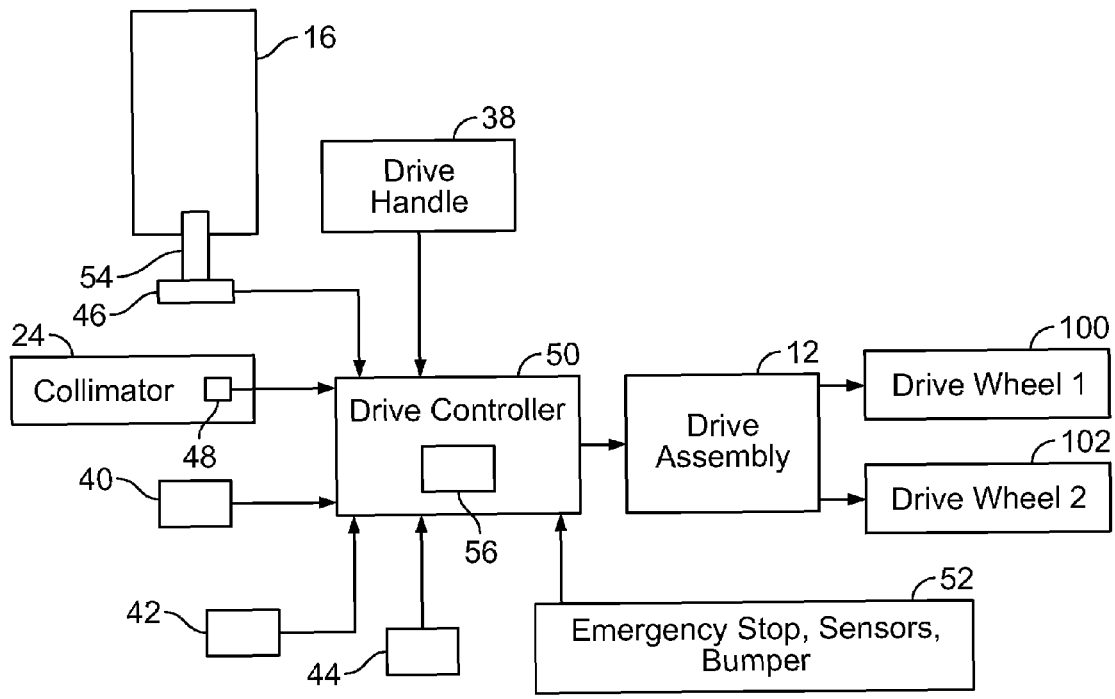
FIG. 2 is a block diagram of the components for rotation-based driving of the system of FIG. 1 in accordance with an embodiment of the present invention.

FIG. 2 is a block diagram of the components for rotation-based driving of the system 10 of FIG. 1. As discussed previously, when moving to another room and during initial positioning, the drive controller 50 receives drive input(s) from the drive handle 38. Based on the drive input(s), the drive controller 50 outputs velocity information to the drive assembly 12 to drive each of first and second drive wheels 100 and 102 (which in one embodiment are the rear drive wheels 18 shown in FIG. 1). At any time during operation, the drive controller 50 may be configured to receive and act upon an input from one or more emergency stop mechanisms 52, which may include one or more of a button, sensor, bumper and the like.

In one embodiment, the bottom of the column 16 is connected to a shaft 54 that extends from the drive assembly 12. The sensor 46 is connected to the shaft 54 to detect the rotation of the column 16. The sensor 46 provides the rotation information to the drive controller 50. It should be understood that other encoder or sensor configurations may be used to sense the rotation of the column 16. The sensor 48 mounted to or proximate the collimator 24 senses rotation of the collimator 24 and provides the rotation information to the drive controller 50. The sensor 46 and the sensor 48 may communicate wirelessly or over wired connections.

When the drive controller 50 receives input from one of the user interfaces 40-44, a rotation-based drive module 56 may determine the velocities for each of the first and second drive wheels 100 and 102 based on the rotation information provided by one or both of the sensors 46 and 48, as well as the particular input from the user interface 40-44.

Figure 3:
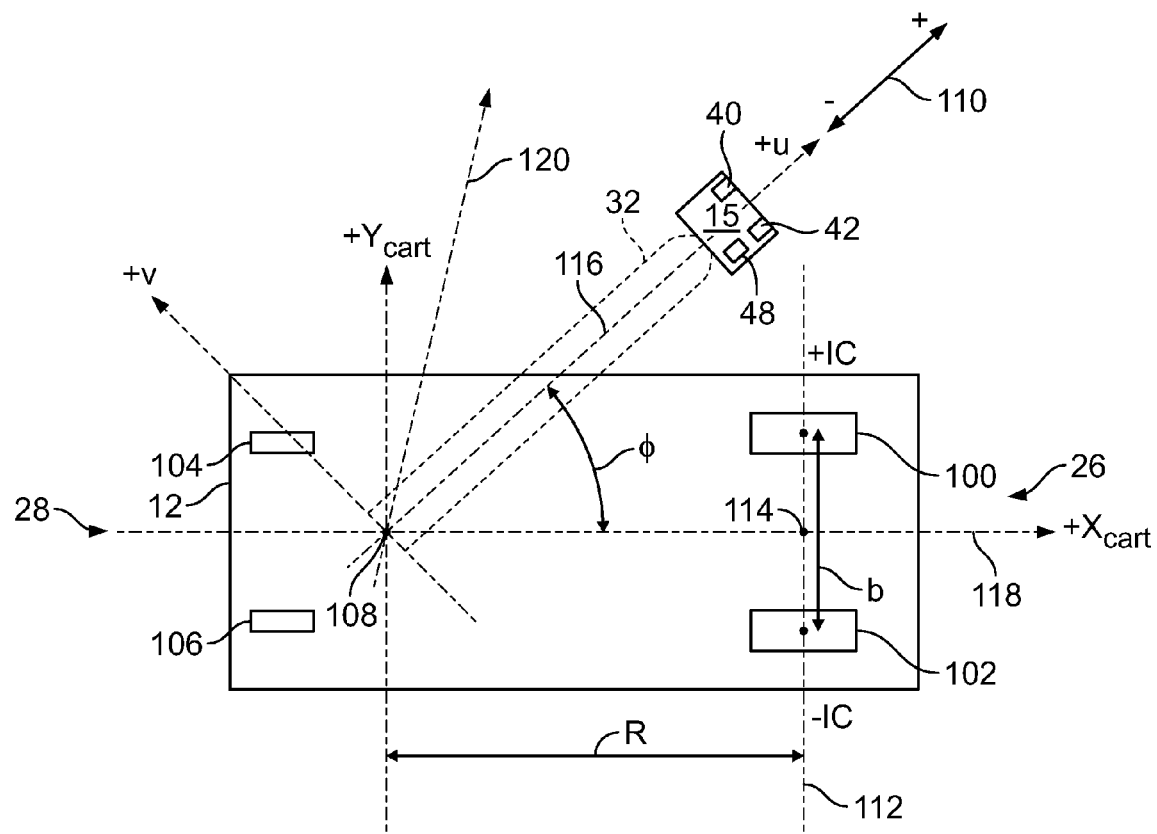
FIG. 3 is a schematic diagram illustrating the orientation of the drive assembly and column with respect to each other in accordance with an embodiment of the present invention.

FIG. 3 is a schematic diagram illustrating the orientation of the drive assembly 12 and column 16 with respect to each other. First and second drive wheels 100 and 102 are shown proximate the rear end 26 of the drive assembly 12. First and second swivel wheels 104 and 106 are shown proximate the front end 28 of the drive assembly 12. A distance b between the first and second drive wheels 100 and 102 is indicated.

The drive assembly 12 may have a coordinate system Xcart, Ycart. Longitudinal axis 118, corresponding to Xcart, extends parallel to the length of the drive assembly 12 and is centered between the first and second drive wheels 100 and 102. The column 16 (not shown) pivots with respect to the drive assembly 12 at pivot point 108. For example, referring to FIG. 2, a center of the column 16 or the shaft 54 may define the pivot point 108. The column 16 may have a coordinate system u, v. The pivot point 108 is the point of origin for both of the coordinate systems. As shown in FIG. 3, the column 16 is pivoted with respect to the longitudinal axis 118 such that a center line 116 of the arm 32 (corresponding to the u axis) is at an angle of rotation (p with respect to the longitudinal axis 118.

The first and second drive wheels 100 and 102 are positioned along drive axis line 112. A distance R is indicated between a center point 114 along the drive axis line 112 between the first and second drive wheels 100 and 102 and the pivot point 108.

By way of example, the operator may have positioned the x-ray source assembly 15 over the subject 29 and wishes or needs to move the x-ray source assembly 15 along the u axis. The positive and negative movement directions along the u axis are indicated with arrow 110. The direction of movement is selected through the user interface 40-44. Movement along the u axis may be accomplished by automatically driving, with the drive assembly 12, the first and second drive wheels 100 and 102 with different velocities based on the angle φ. The velocity includes a speed component, which may be measured, for example, in millimeters (mm) per second, and a direction component (e.g., forward and backward). Forward may be defined as towards the front end 28 of the drive assembly 12 and backward may be defined as towards the rear end 26 of the drive assembly 12.

By driving the first and second wheels 100 and 102 with different velocities, the drive assembly 12 will rotate about an instant center (IC), which is located at some point along the drive axis line 112. For example, if the speed at each of the first and second drive wheels 100 and 102 is equal but in opposite directions, then the IC equals 0, which is the center point 114 between the two wheels 100 and 102. Positive values of IC are located along the drive axis line 112 to the side of the first drive wheel 100 and negative values of IC are located along the drive axis line 112 to the side of the second drive wheel 102. If the velocity at the first drive wheel 100 is zero and the velocity at the second drive wheel 102 is not zero, then IC equals b/2, which is located at the first drive wheel 100. If the velocity at the first drive wheel 100 is not zero and the velocity at the second drive wheel 102 is zero, then IC equals −b/2 and is located at the second drive wheel 102.

When the operator activates one of the user interfaces 40-42, the rotation-based drive module 56 determines the velocities of the first and second drive wheels based on the following equations:

$$V_1 = b * V_t * \sin \phi / 2R - V_t * \cos \phi \quad \text{Eq. 1}$$

$$V_2 = -b * V_t * \sin \phi / 2R - V_t * \cos \phi \quad \text{Eq. 2}$$

wherein $V_1$ and $V_2$ are velocities of the first and second drive wheels 100 and 102, respectively. When V is positive, the associated drive wheel is driven forward and when V is negative, the associated drive wheel is driven backward. The distance between the first and second drive wheels 100 and 102 is b, R is the distance between the drive axis line 112 and the pivot point 108 of the column 16, and $V_t$ is the desired velocity (magnitude and direction) at the pivot point 108.

As shown in FIG. 3, φ is the angle of rotation of the column 16 with respect to the longitudinal axis 118. However, φ may be selected to be along the v axis, such as by selecting an input on the user interface 40-44, and the drive controller 50 effectively calculates the angle by adding 90 degrees to the angle of the column 16 (φ as shown in FIG. 3). Other driving directions may be achieved, such as by determining φ based on the angle of rotation of the column 16 as well as the angle of rotation of the collimator 24. For example, the collimator sensor 48 may detect motion of the collimator with respect to the u axis. The user interface 40-44 may provide an input that allows the operator to select motion along a forward or negative collimation direction, which may be along one of the u or v axis, or may along neither of the u or v axis, such as along line 120. In another embodiment, φ may be based on the angle of rotation of the collimator 24 with respect to the column 16 or the drive assembly 12. Also, the plurality of buttons on the user interface 40-44 may provide an ability to select various system components and/or directions to be used when determining the angle φ. By way of example only, the user interface 40-44 may provide different buttons for requesting movement along each of the Xcart, Ycart, u and v axis.

Returning to the example of FIG. 3, to move in the positive direction of arrow 110, the velocity $V_t$ is positive. $V_t$ may be slower than the velocity that is allowed when the system 10 is driven longer distances using the drive handle 38, such as from one room to another. In one embodiment, the magnitude of $V_t$ may be set to a predetermined number such as to achieve a maximum movement, for example, of 100 mm per second or 50 mm per second. It should be understood that the magnitude of $V_t$ may be set to achieve other speeds. In another embodiment, the magnitude of $V_t$ may vary based on the angle of rotation φ wherein $V_t$ is faster within some predetermined range of φ.

When the first and second drive wheels 100 and 102 are driven at different velocities based on the angle of rotation φ, the drive assembly 12 rotates about an IC located along the drive axis line 112 and the pivot point 108 moves along the u axis (or other selected axis or direction). The operator may disengage the brake on the column 16 as the drive assembly 12 is driven, allowing the column 16 to rotationally "float". The operator may then manually adjust the angle of rotation φ between the column 16 and the longitudinal axis 118 to either maintain motion along the u axis or change the direction of motion. As the angle of rotation φ changes, the rotation-based drive module 56 dynamically recalculates the velocities for each of the first and second drive wheels 100 and 102 such that the pivot point 108 continues to move along the u axis or other desired travel direction. As the angle of rotation φ changes, the drive assembly 12 may rotate about a different IC.

The dynamically changing velocities may be applied to the first and second drive wheels 100 and 102 for a predetermined amount of time, such as five seconds or a predetermined travel distance. The operator may then need to select or activate one of the user interfaces 40-42 to move the unit an additional distance. In another embodiment, the rotation-based drive module 56 may calculate the velocities and move one or more of the first and second drive wheels 100 and 102 while the operator holds the user interface 40-42 in an "on" position. The rotation-based drive module 56 stops the motion when the user interface 40-42 is in an "off" position. In one embodiment, the column 16 may be locked when the operator selects the user interface 40-44. The drive assembly 12 may have a column drive mechanism (not shown) that may automatically adjust the angular position of the column 16 with respect to the longitudinal axis 118 to maintain the angle of rotation φ.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A mobile imaging system, comprising:
    a motorized drive assembly;
    first and second drive wheels coupled to the motorized drive assembly;
    a column coupled to and extending upwardly from the motorized drive assembly, the column rotatable around a pivot point;
    an arm coupled to the column, the arm including a radiation source mounted on an outer end thereof;
    a longitudinal axis extending parallel to a length of the motorized drive assembly and centered between the first and second drive wheels; and
    a controller configured to determine first and second velocities to drive the first and second drive wheels based on an angle of rotation of the column with respect to the longitudinal axis.

2. The system of claim 1, wherein the controller is further configured to dynamically change at least one of the first and second velocities as the angle of rotation of the column changes.

3. The system of claim 1, further comprising at least one user interface, the controller further configured to receive an input from the at least one user interface, the input indicating a request for movement of the first and second drive wheels to move the mobile imaging system based on the angle of rotation of the column.

4. The system of claim 1, further comprising a user interface, the controller further configured to receive an input from the user interface, the input indicating one of a request for movement of the first and second drive wheels based on the angle of rotation of the column and a request for cessation of movement of the first and second drive wheels.

5. The system of claim 1, wherein the controller further determines the first and second velocities based on at least one of a distance between the first and second drive wheels and a desired velocity.

6. The system of claim 1, wherein the controller further determines the first and second velocities based on a distance along the longitudinal axis between the pivot point and the first and second drive wheels.

7. The system of claim 1, wherein the first and second velocities comprise a direction component and a speed component.

8. The system of claim 1, wherein the radiation source is an x-ray source.

9. The system of claim 1, further comprising at least one user interface configured to request movement of the first and second drive wheels based on the angle of rotation, the at least one user interface comprising at least one of a button, a toggle switch, a joystick, a power assist handle, a keyboard, a touchscreen and a remote control.

10. The system of claim 1, further comprising a sensor mounted proximate to the column, the sensor detecting the angle of rotation of the column.

11. A method for driving a mobile imaging system, the method comprising:
    defining a longitudinal axis that is centered between first and second drive wheels of a motorized drive assembly and is parallel to a length of the motorized drive assembly;
    defining a pivot point at a center of a rotatable column that is coupled to the motorized drive assembly, the column comprising an arm mounted thereto;
    identifying an angle of rotation of the column with respect to the longitudinal axis; and
    calculating first and second velocities to drive the first and second drive wheels based on the angle of rotation.

12. The method of claim 11, further comprising:
    receiving a request for movement based on the angle of rotation; and
    driving the first and second drive wheels for one of a predetermined time and a predetermined distance.

13. The method of claim 11, wherein the first and second velocities are further calculated based on at least one of a distance between the first and second drive wheels and a predetermined velocity at the pivot point.

14. The method of claim 11, wherein the first and second velocities are further calculated based on a distance along the longitudinal axis between the pivot point and the first and second drive wheels.

15. A mobile x-ray system, comprising:
    a motorized drive assembly comprising first and second drive wheels;
    a column mounted to the motorized drive assembly at a pivot point, the column comprising an arm mounted thereto, the column rotatable with respect to the pivot point;
    a longitudinal axis extending parallel to a length of the motorized drive assembly and centered between the first and second drive wheels;
    an x-ray source mounted at an outer end of the arm;
    a collimator mounted with respect to the x-ray source, the collimator being rotatable with respect to the x-ray source; and
    a controller configured to determine first and second velocities to drive the first and second drive wheels, the first and second velocities based on at least one of an angle of rotation of the column with respect to the longitudinal axis and an angle of rotation of the collimator with respect to the longitudinal axis.

16. The system of claim 15, further comprising a sensor mounted with respect to the column, the sensor detecting rotation of the column.

17. The system of claim 15, further comprising a sensor mounted proximate to the collimator, the sensor detecting rotation of the collimator.

18. The system of claim 15, further comprising a user interface for activating motion of the first and second drive wheels based on the angle of rotation.

19. The system of claim 15, further comprising a user interface for activating motion of the first and second drive wheels based on the angle of rotation, the user interface being configured to receive motion requests for at least two different directions.

20. The system of claim 15, wherein the first and second velocities drive the first and second drive wheels, respectively, to move the mobile x-ray system along a straight line extending from the pivot point along at least one of the angle of rotation of the column and the angle of rotation of the collimator.

* * * * *